(12) United States Patent
Hanna et al.

(10) Patent No.: US 7,583,861 B2
(45) Date of Patent: Sep. 1, 2009

(54) INTELLIGENT MEDICAL IMAGE MANAGEMENT SYSTEM

(75) Inventors: Christopher J. Hanna, Fox Point, WI (US); Timothy J. O'Connor, Franklin, WI (US)

(73) Assignee: Teramedica, Inc., Milwaukee, WI (US)

( * ) Notice: Subject to any disclaimer, the term of this patent is extended or adjusted under 35 U.S.C. 154(b) by 758 days.

(21) Appl. No.: 10/720,799

(22) Filed: Nov. 24, 2003

(65) Prior Publication Data

US 2004/0141661 A1 Jul. 22, 2004

Related U.S. Application Data

(60) Provisional application No. 60/429,612, filed on Nov. 27, 2002.

(51) Int. Cl.
*G06K 9/00* (2006.01)

(52) U.S. Cl. .................................................. 382/305

(58) Field of Classification Search ........................ None
See application file for complete search history.

(56) References Cited

U.S. PATENT DOCUMENTS

| | | | |
|---|---|---|---|
| 5,058,185 A * | 10/1991 | Morris et al. ............... | 382/305 |
| 5,165,011 A * | 11/1992 | Hisano ......................... | 706/50 |
| 5,305,438 A | 4/1994 | MacKay et al. | |
| 5,321,520 A | 6/1994 | Inga et al. | |
| 5,586,262 A | 12/1996 | Komatsu et al. | |
| 5,655,084 A | 8/1997 | Pinsky et al. | |
| 5,668,998 A | 9/1997 | Mason et al. | |
| 5,671,353 A | 9/1997 | Tian et al. | |
| 5,740,428 A | 4/1998 | Mortimore et al. | |
| 5,774,661 A | 6/1998 | Chatterjee et al. | |
| 5,802,253 A | 9/1998 | Gross et al. | |
| 5,818,467 A | 10/1998 | Schimitzek | |
| 5,974,201 A | 10/1999 | Chang et al. | |
| 6,006,191 A | 12/1999 | DiRienzo | |
| 6,260,021 B1 | 7/2001 | Wong et al. | |
| 6,289,115 B1 | 9/2001 | Takeo | |
| 6,349,330 B1 | 2/2002 | Bernadett et al. | |
| 6,351,547 B1 | 2/2002 | Johnson et al. | |
| 6,418,475 B1 * | 7/2002 | Fuchs ........................... | 709/238 |
| 6,424,996 B1 | 7/2002 | Killcommons et al. | |
| 6,427,032 B1 * | 7/2002 | Irons et al. ................... | 382/306 |
| 6,574,742 B1 * | 6/2003 | Jamroga et al. .............. | 713/400 |
| 2002/0013915 A1 * | 1/2002 | Migita et al. ................. | 714/6 |
| 2002/0059300 A1 | 5/2002 | Nagata et al. | |
| 2002/0073429 A1 | 6/2002 | Beane et al. | |

FOREIGN PATENT DOCUMENTS

WO WO 01/35310 A1 5/2001

* cited by examiner

*Primary Examiner*—Matthew C Bella
*Assistant Examiner*—Alex Liew
(74) *Attorney, Agent, or Firm*—Quarles & Brady, LLP

(57) ABSTRACT

An image management system connects to a health care enterprise intranet and receives images from medical imaging devices located throughout the enterprise. The image management system also receives images, patient information and administrative information from PAC, RIS and HIS systems. The images are automatically archived in a number of storage devices having different cost and performance characteristics in accordance with a set of stored health care enterprise rules.

32 Claims, 9 Drawing Sheets

JMS MESSAGE

INTELLIGENT MEDICAL IMAGE MANAGEMENT SYSTEM

CROSS-REFERENCE TO RELATED APPLICATIONS

This application claims the benefit of U.S. Provisional Application No. 60/429,612 filed Nov. 27, 2002.

BACKGROUND OF THE INVENTION

The field of the invention is systems for storing and managing medical images for a health care enterprise.

Medical images are acquired by a large number of different imaging modalities, including X-ray imaging, computed tomography X-ray, radioisotope emission imaging, computed emission tomography, magnetic resonance imaging and ultrasonic imaging. Current computer systems for storage, retrieval and viewing of digital medical images (referred to as Picture Archiving and Communication, or "PAC", systems), typically have limited amounts of digital storage, a processor for storing and indexing images, and user workstations attached directly, or across a network, to the PAC systems for image display. These PAC systems are usually designed with a client-server structure. In such structures, the workstations, acting as image clients, run specific software designed for interacting with a specific PAC system, acting as an image server, in order to obtain and display images. The specific server software on the PAC system is designed to accept and respond only to the specific requests from the corresponding image-clients.

PAC systems are quite satisfactory for use throughout a single department (e.g., radiology) in a hospital, but difficulties arise when managing images from multiple modalities or different PAC systems used throughout a hospital or used throughout multiple hospitals in a large health care enterprise. A user needing access to images from multiple modalities on different PAC systems needs specific client software suited for each PAC image server.

In addition to image data, text information is also captured and stored by health care enterprises. Such information includes patient information, information regarding the image acquisition, and medical assessment information regarding a patient's medical condition based on an evaluation of the image. This textual information is captured by Radiology Information ("RIS") systems, and like PAC systems, RIS systems are usually designed as a client-server system which requires particular client software for the work station. Thus, it is not likely that information can be exchanged between RIS systems from different manufacturers and it is even less likely that information can be exchanged between a PAC and RIS system.

There are also other information storage systems in typical health care enterprises. For example, there are specialized department systems, such as those for storing and retrieving diagnostic cardiology images, for interfacing to and reporting results from laboratory instruments, for pharmacy management, and so forth. There are also institution-scale Hospital Information ("HIS") systems, such as those for patient financial and billing, or for patient admissions, discharge, and transfer ("ADT").

All of these systems, like PAC and RIS systems, comprise specialized software designed for the particular application. And like PAC and RIS systems, these departmental or institution-scale information systems are not interoperable and cannot exchange data. Users typically require separate client software to interface with each of these systems.

Efforts have been made to standardize data objects handled by PAC systems to ameliorate the incompatibility problem. For example, the Digital Imaging and Communications in Medicine ("DICOM") standard relevant to medical image distribution has been developed and promoted by the American College of Radiology/national Equipment Manufacturers Association (ACR/NEMA). DICOM aims to standardize formats for exchange of image data in PAC systems by defining a standard set of basic and composite data types along with a standard set of services involving those data types, all of which are representative of the imaging activities in a radiology department. Accordingly, a single workstation with a DICOM-conforming client can expect some success in accessing PAC systems from different manufacturers. Individual variations in the details of DICOM-conformance, however, may still defeat interoperability or data interchange in some instances.

A similar standard applicable to RIS systems is HL/7, a standard that aims to define formats for electronic data interchange in health-care environments. In particular, HL/7 defines message formats for exchange of information relating to a broad range of health care activities, including patient admission, discharges, transfers, patient queries, billing, clinical observations, and orders, and eventually patient medical records generally. Because of such broad goals, HL/7 is less of a true "plug-and-play" standard than is DICOM. In other words, two systems, although conforming to HL/7, may not be able to exchange requests and data. Therefore, a single user may still require multiple clients in order to access multiple RIS systems, even though they are all HL/7 conforming. In addition, even within one radiology department a DICOM-conforming PAC system cannot exchange service requests or data with an HL/7-conforming RIS system. The problem of using information and images from such a wide variety of sources has been addressed by systems such as that disclosed in U.S. Pat. No. 6,260,021, but such distribution systems do not address the storage of images from the wide array of devices found in a typical health care enterprise.

The storage of a large number of images and associated textual information is a complex and costly undertaking. A typical PAC system has a high speed memory which stores acquired images and makes those images available to a compatible work station. On-line memories with disk storage units using RAID technology are usually provided for such short term storage. These are relatively costly and usually they have limited storage capacity. However, RAID technology provides fast access to the images. In view of these characteristics of RAID technology, after diagnostics is performed on the image by a radiologist, the image is typically removed from the PAC system storage and archived. In the past, images were routinely archived as a film or a print out, but increasingly, images are stored in machine-readable form on magnetic tape or optical discs according to rules established by the health care enterprise. Such rules are intended, of course, to keep the images and associated textual information readily available for use while the patient is undergoing diagnosis or treatment and to archive the same to larger and less costly storage means when reasonably possible.

Consolidation in the health care industry has resulted in the formation of large, geographically widespread health care systems. These systems offer their patients high quality care and cost efficiency resulting from economies of scale. Health care systems achieve the full benefit of their economies of scale by providing an integrated network for the delivery of patient services. This means that specialized medical services, including imaging services, are leveraged across all departments and all locations. This is not achieved with current systems, however, in which images are stored on department PACs at each location and images are archived by each department on film or tape.

Advances in medical imaging technologies is compounding the problem of image distribution, storage and archiving. Medical imaging now reaches far beyond its traditional roots in Radiology. Today imaging procedures are standard diagnostic tools in Cardiology, Endoscopy, Ophthalmology, Pathology, Surgery, Dentistry and more. Unfortunately digital image management technology has not progressed much beyond its traditional roots in radiology PAC systems. In fact these systems have yet to fully master the multi-modality requirements of radiology. Sophisticated image management across all departments and specialties of the clinical practice is unknown. In addition, new digital imaging systems produce more studies per hour and more image data per study than traditional analog imaging modalities, thus further magnifying the economic and patient service issues.

Because of advances in digital storage technology film is no longer the medium of choice for archiving diagnostic images. Digital image storage is subject to lower rates of loss or damage, and studies have shown a 70 to 85% reduction in cost over film-based systems. To achieve such cost reductions, however, it is imperative that available digital data storage capacity be intelligently used. Table 1 lists example storage devices, the cost to store data in such devices based on current device purchase prices and the average retrieval time of images from the devices.

TABLE 1

| Storage Device | Cost per MB ($USD) | Average Retrieval Performance (MB/sec) |
| --- | --- | --- |
| RAID | .06–.40 | 50 |
| Tape | .02–.08 | 15 |
| Optical CD/DVD | .001–.01 | 3.6 |

It is apparent from Table 1 that there is a tradeoff between storage cost and image retrieval time. To drive the overall storage cost down, therefore, the health care enterprise will make business decisions regarding which images will be stored in faster, higher cost devices and which will be archived to slower, low cost devices or media. For example, a radiology department may have a policy of archiving images compressed in a lossless manner stored on a RAID device to magnetic tape compressed in a lossless manner one year after the image is acquired.

A complicating factor when managing images across an entire health care enterprise is that image storage policies are not uniform. Storage policies may differ, for example, based on the imaging modality used (i.e., MRI, CT, PET, etc.), the subject of the study (i.e., head, abdomen, etc.), and the department from which the image originates (i.e., Radiology in hospital A, Radiology in hospital B, Cardiology in clinic C, etc.). The intelligent management of medical images thus requires a system which stores images acquired from many different sources throughout the enterprise, and stores the images on media and in a form that is most cost effective and in accordance with enterprise policies. The system also retrieves images from storage and delivers those images and associated textual information to workstations throughout the enterprise regardless of the particular standards or protocols that are used to acquire the images or information.

SUMMARY OF THE INVENTION

The present invention is an image management system for receiving images from a wide variety of imaging devices, evaluating and storing metadata associated with each image using a set of stored rules that embody the enterprise image storage policies, and storing the images in storage devices having different cost and performance characteristics in accordance with rules established by the enterprise.

A general object of the invention is to intelligently and automatically store large number of images in accordance with enterprise policies. Such policies may, for example, take into consideration when the image was acquired, which device acquired the image, where the acquiring device is located, the subject of the image, the time of day, the date, the amount of storage space available, etc. These evaluation parameters are entered as a set of rules which are stored in the image management system and used to evaluate how each incoming image is to be stored.

Another object of the invention is to efficiently evaluate and store incoming images. Metadata associated with each image is separated from the image and used in the evaluation process. The large image data files are temporarily held in buffer storage and transferred directly to the storage device after the metadata is evaluated. Unnecessary transfers of the large image files are thus avoided. The metadata is separately stored in a database where it can be readily retrieved regardless of which storage device its associated image data is archived in.

Another object of the invention is to authenticate not only users of the image management system but the imaging devices which submit images to the system. This is accomplished by an enterprise authority manager which stores both user profiles and device profiles. Servers which receive images and/or information access the profiles to determine quickly whether the requested service is authorized.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
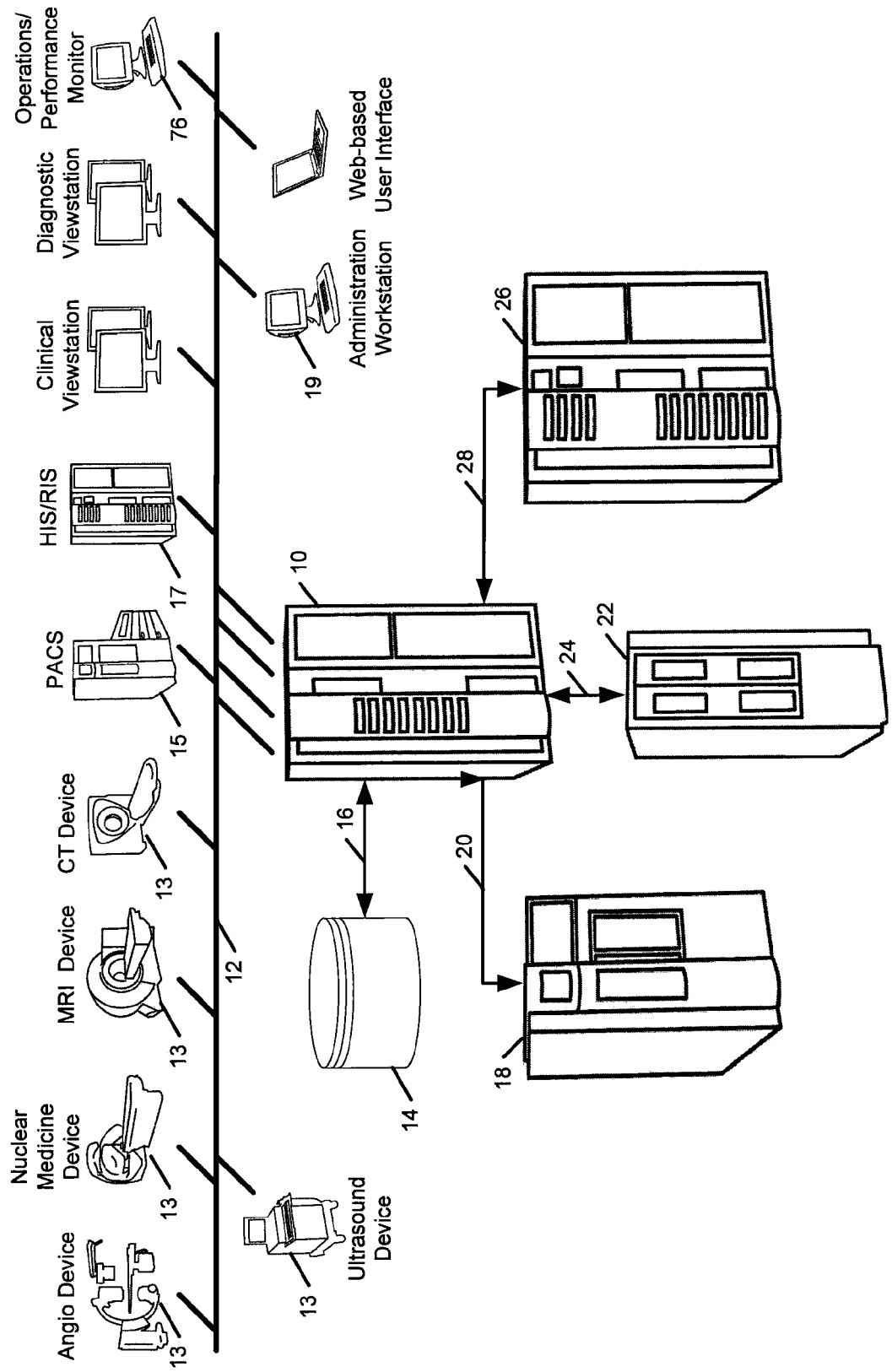
FIG. 1 is a pictorial view of a preferred embodiment of the image management system connected to a health care enterprise intranet.

Referring particularly to FIG. 1, an intelligent image management system 10 connects to devices located throughout a health care enterprise through a high speed serial communication network, or "intranet" 12. in the preferred embodiment a so-called Ethernet communications network which complies with the IEEE 802.3 standard communications protocol is employed and the TCP/IP network protocol is employed. Bridges (not shown in the drawings) may also connect the intranet 12 to the Internet to communicate with remote devices such as personal computers located in a physician's office or home.

Figure 2:
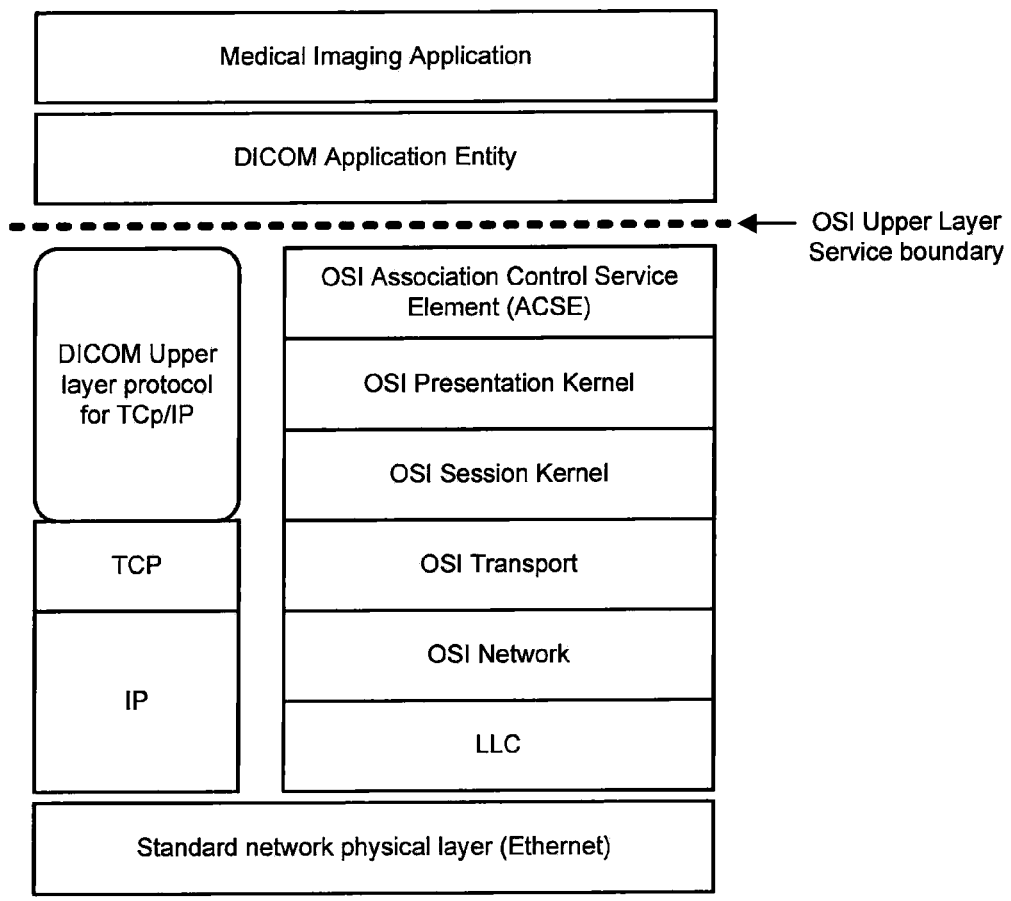
FIG. 2 is a schematic representation of the DICOM communications protocol used to transfer medical images on the intranet in the system of FIG. 1.

A wide variety of devices may communicate with the intelligent image management system 10, including imaging devices 13 commonly found in hospitals and clinics. These devices 13 will normally employ the Digital Imaging and Communications in Medicine (DICOM) standard that establishes a protocol, syntax and semantics of commands and associated information that must be supplied to insure interoperability with other DICOM compliant devices. The DICOM compatible submission of images to the intelligent image management system 10 is illustrated in FIG. 2 as it relates to the ISO communications model. DICOM is also the communications protocol used with Picture Archiving and Communications (PAC) systems 15 maintained by departments in the health care enterprise for storing images.

Figure 3:
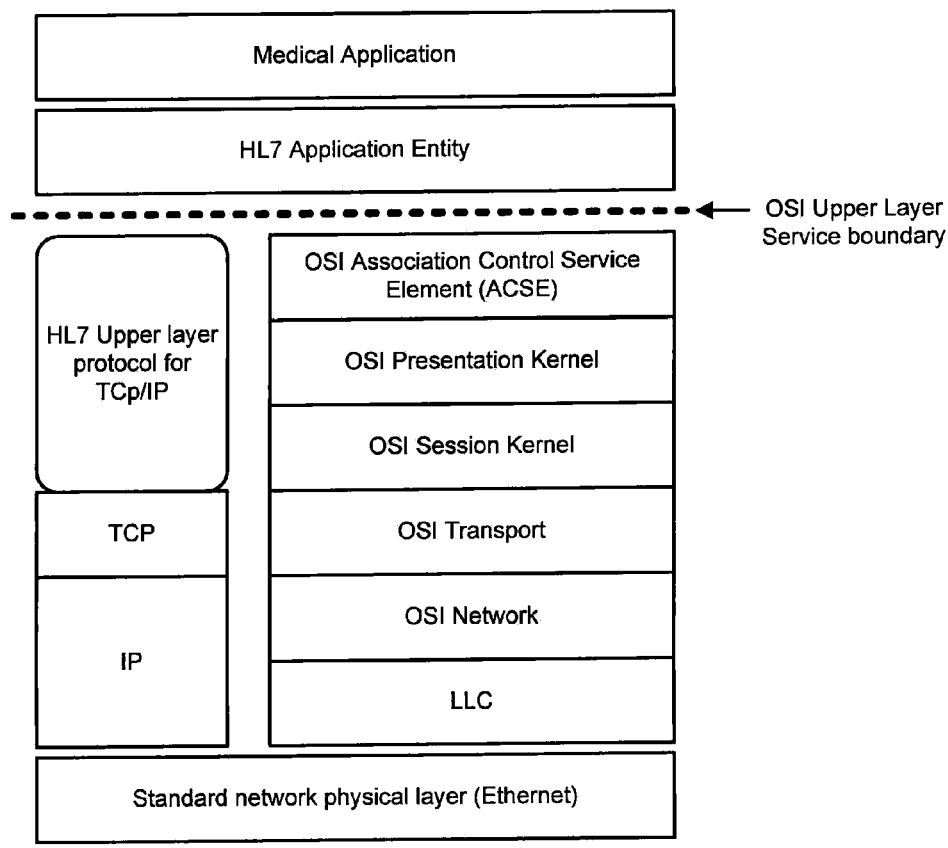
FIG. 3 is a schematic representation of the HL/7 communications protocol used to transfer patient and administration information on the intranet in the system of FIG. 1.

The intranet 12 may also connect to one or more computer systems that support clinical patient care as well as the management, delivery and evaluation of health care services by the enterprise. These include RIS and HIS systems 17 which employ the HL/7 standard protocol, as well as administrative workstations 19 that are used with such systems. As with DICOM, the HL/7 standard establishes the upper layers of the protocol used to communicate with the intelligent image management system 10 as shown in FIG. 3.

The intranet 12 also supports WEB-based devices that employ Hyper Text Transfer Protocol (HTTP) to exchange data of various content, including Hypertext Transfer Markup Language (HTML) documents, plane text documents, images, graphics and extensible Markup Language (XML) documents. Such devices include desktop personal computers, laptop personal computers, PDAs and the like which employ a browser such as that sold under the trademark Microsoft Internet Explorer to communicate on the intranet 12. One aspect of the present invention is that such general purpose personal computers can be intelligently, automatically optimized for viewing medical images and other associated information by downloading to the browser through the intranet 12 applets that enable the full capabilities of the personal computer to be used.

Other communications protocols may also be supported by the intranet 12 and in many large enterprises there are one or more computer systems which employ special purpose protocols. As will be described below, in such cases the intelligent image management system 10 employs customized server software to support such protocols.

Referring still to FIG. 1, the intelligent image management system 10 connects to four separate data storage devices through cabling, interface circuits and driver software appropriate to each storage device. The first is a hard disk 14 connected to the system 10 through link 16. As will be described in detail below, it is accessed through a database management system and it stores all non-image information such as patient information, management information and textual information associated with images which is referred to herein as "metadata". Although storage device independent, in a typical installation multiple, 72.8 gigabyte hard drives manufactured by IBM Corporation are employed to store such data. In the set of storage devices available to the system 10 the hard disk 14 is characterized by the highest cost per megabyte of storage and by the fastest data access speed.

Image data is stored on three types of storage devices. The first is a Redundant Array of Inexpensive Drives (RAID) mass storage device 18 which connects through link 20 and provides on-line storage of image data. The RAID storage device 18 is comprised of dual sets of interface, controller, and drive modules allowing simultaneous input through one set of interface, controller and drive module, and output through the other set. Furthermore, each set of interface, controller and driver module allows a high rate of data transfer in the order of tens of mb/sec. For further description of RAIDs, see E. K. Lee, *Software and Performance Issues in the Implementation of a RAID Prototype*, Report No. UCB/CSD 90/573, Computer Science Division, U. of California at Berkeley, 1990. In the preferred embodiment a commercially available RAID storage device such as the Total Storage Enterprise Storage Server from IBM Corporation having a capacity typically in the range of 2.5 to 30 terabytes provides relatively expensive "on-line" storage of image data.

The second class of image storage devices is a DVD library storage device 22 connected through link 24. The DVD library storage device 22 contains shelves, or "slots", which hold digital video disks, or DVD. One or more drives are housed in the storage device 22 and one or more robot picker and transport assemblies move the storage disks between the shelves and the drives. The storage device 22 provides "on-line" access to images on disks inserted into its drives and it provides "in-line" access (i.e., 2 to 5 seconds) to images on disks in its shelves. In the preferred embodiment a DVD library commercially available from Pioneer Electronics and having a storage capacity in the range of 0.25 to 3.38 terabytes is employed.

The third class of image storage devices is an automated tape library 26 connected to system 10 through a link 28. The storage device 26 has storage cells for tape cartridges and a robotic accessory which transports tape cartridges between one or more tape drives. Access time for an image on a tape cartridge in the storage device is 13 seconds on average and thousands of tape cartridges can be managed providing image data storage in the 100s of terabytes. In the preferred embodiment an automated tape library commercially available from Storage Tek is employed. The tape library storage device 26 is characterized as the lowest cost choice for image storage with a relatively long access time.

It should be apparent that the intelligent image management system 10 supports a variety of storage devices using technologies that provide a wide range of cost and performance choices. It is an objective of the system 10 to make these choices in a cost effective manner and in accordance with established enterprise policies. Storage is a dynamic technology with a rapid pace of innovation and improvement in price/performance. The intelligent image management system allows the business enterprise to rapidly adopt storage innovations and dynamically adjust usage management policies through a set of stored rules described in detail below.

The intelligent image management system 10 is a programmed general purpose digital computer having Ethernet network interface cards (not shown) that connect it to the intranet 12 and interface cards (not shown) that connect it through links 16, 20, 24 and 28 to the respective storage devices 14, 18, 22 and 26. The selection of computer depends on the size of the enterprise and in the preferred embodiment a midrange server sold under the trademark SunFire 3800 server by Sun Microsystems, Inc. is employed. It typically employs from 6 to 8 processors and from 2 to 8 gigabytes of random access memory. The operating system sold by Sun Microsystems, Inc. under the trademark Trusted Solaris 8 is used, as is the JAVA™ 2 Platform Software also available from Sun Microsystems, Inc. One or more JAVA™ virtual machines are established by this software, and as will be described in detail below, most of the functions performed by the intelligent image management system 10 are carried out in response to JAVA™ programs executing in the JAVA™ virtual machine environment.

Figure 4:
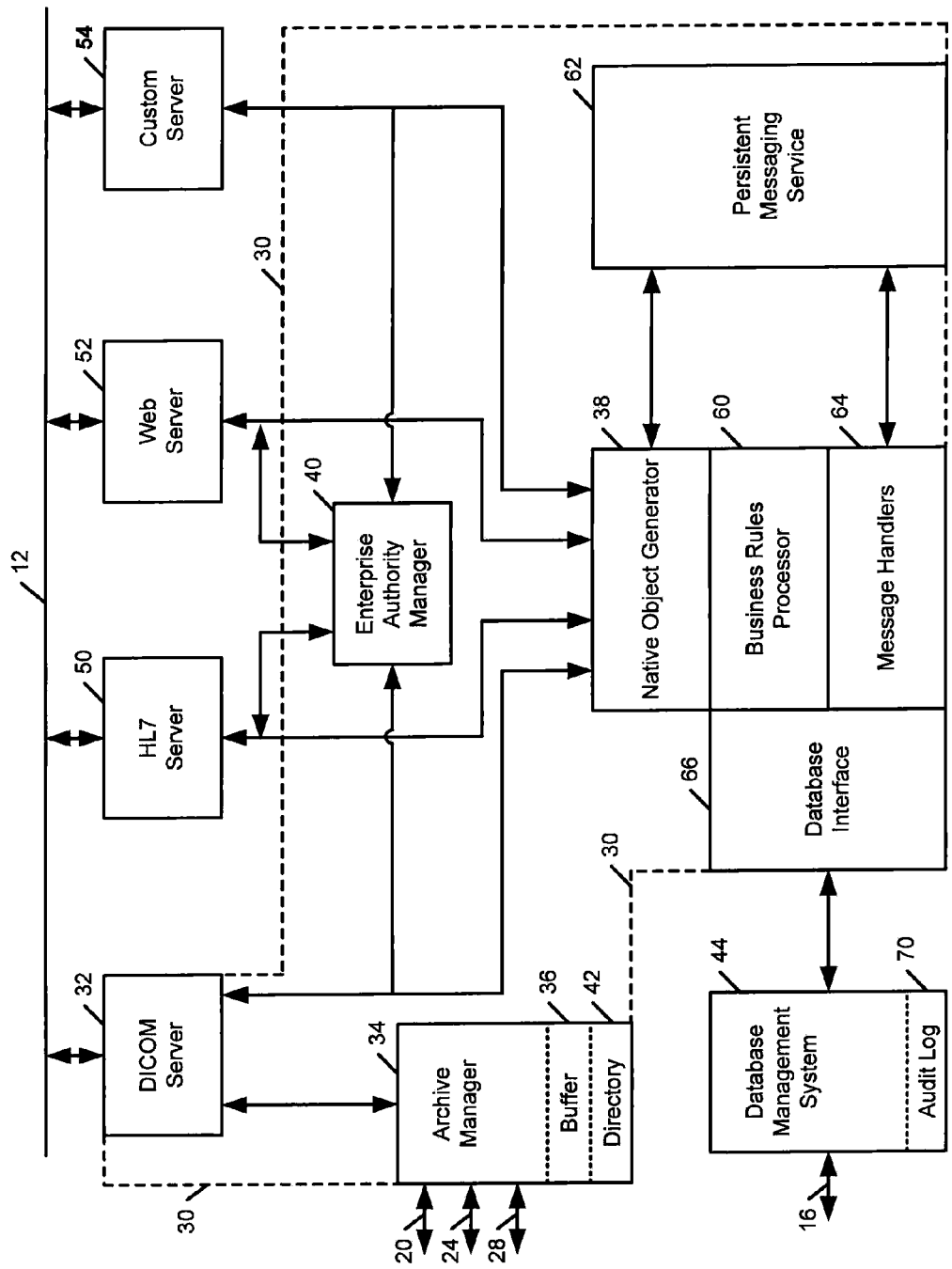
FIG. 4 is a block diagram of the software architecture of the image management system in FIG. 1.

Referring particularly to FIG. 4, the operation of the intelligent imaging system 10 is carried out under the direction of stored software depicted as functional blocks. Those programs executing in a JAVA™ virtual machine environment are indicated by dashed line 30. This software will now be described.

Messages sent to the system 10 using the DICOM standard are received by a DICOM server 32 which is a JAVA™ program that implements the DICOM protocol discussed above and illustrated in FIG. 2. It attends to the performance of services indicated by commands contained in received DICOM messages. It also sends DICOM messages to other DICOM devices on the intranet 12. One of these DICOM services is the storage of image data in a received DICOM message. When this command is detected, the DICOM server 32 forwards the accompanying image data to an archive manager 34 which temporarily stores the data in a buffer memory 36. The archive manager 34 also examines the data and identifies the boundary therein between the image data and the associated, textual metadata. Using this boundary information, the DICOM server 32 forwards the metadata only to a native object generator 38 and an enterprise authority manager 40 for analysis. As will be described in detail below, after the metadata is analyzed, a message is received back through the native object generator 38 indicating where the image in buffer storage 36 is to be stored. This information is relayed to the archive manager 34 which carries out the command by writing the image data to the indicated storage device 18, 22 or 26 through the corresponding link 20, 24 or 28. The archive manager 34 also receives information from a business rules processor 60 indicating the amount of data compression to be applied to the archived image data. The archive, manager 34 also saves folders in a directory 42 indicating all the stored or archived images for each patient. As will be described in more detail below, the textual metadata associated with the stored image data is stored separately in hard drive 14 by a data base management system 44.

The DICOM server 32 is also responsive to messages which request the retrieval of images. When such a retrieval command is detected, the associated information object is sent by the DICOM server 32 to the enterprise authority manager 40 and the native object generator 38 for analysis. As will be described in more detail below, the metadata associated with the requested images is read from the hard drive 14 and returned to the DICOM server 32. Information is then passed to the archive manager which uses that and information in the directory 42 to retrieve the requested images from storage and hold them in buffer 36. The DICOM server 32 is signaled that the images have been retrieved and the server 32 constructs and sends a responsive DICOM message on intranet 12 containing the retrieved images.

One unique characteristic of the intelligent image management system 10 is the separate and direct handling of the large image files. Images files are not passed between functional elements of the system, but are instead, held in the buffer 36 while processing and analysis is conducted on the associated textual metadata. The associated metadata is also stored separately from the archived images on hard drive 14 and is accessible using a sophisticated database management system 44. This enables information regarding archived images to be quickly retrieved in response to DICOM query commands or in response to requests from HIS or RIS systems. Large image files are thus not needlessly retrieved or moved about in the system 10.

Referring particularly to FIG. 4, an HL/7 server 50 is a software module written in C and $C^{++}$ which implements the HL/7 protocol discussed above and illustrated in FIG. 3. The HL/7 server 50 listens for HL/7 messages from PAC, HIS and RIS systems and passes information therein to the enterprise authority manager 40 and the native object generator 38. Such HL/7 messages do not include images, but instead, contain textual information regarding patients. For example, an HL/7 message may identify a patient who has checked into the facility and is scheduled for an MRI examination the next day. Such information is stored in a master patient index on the hard drive 14 by the database management system 44. Similarly, the HL/7 server 50 sends messages to devices connected to the intranet 12 using the HL/7 protocol. For example, in response to an inquiry from an HIS system, information on a patient may be read from the hard disk 14 and coupled to the HL/7 server 50. The server 50 packages this information in a form compatible with the HL/7 protocol and sends the message on the intranet 12.

A WEB server 52 also connects the intelligent image management system 10 to the intranet 12. It is formed around a commercially available WEB server program such as Microsoft Corporation's Internet Information Server which exchanges data with a commercially available browser such as Microsoft Corporation's Internet Explorer running on another device connected to the intranet 12. Programs written in C and $C^{++}$ convey messages received by the WEB server 52 to the enterprise authority manager 40 and the native object generator 38. These programs also receive information back from the enterprise authority manager 40 and native object generator 38 and packages it in a message format for transmission on the intranet 12.

When a WEB-based device makes a request for services from the intelligent image management system 10, the WEB server 52 responds by interrogating the requesting device for information regarding its identity. The WEB server 52 then retrieves information related to the capabilities of the WEB-based device from the enterprise authority manager 40. For example, the size and resolution of its display are of particular importance when formatting data. The WEB server 52 then downloads to the WEB-based device a JAVA™ applet which takes advantage of all the performance capabilities of the device during the subsequent session in which information is exchanged.

Additional servers, such as custom server 54 may also convey messages between devices connected to intranet 12 and the intelligent image management system 10. As with the other servers 32, 50 and 52, the custom server 54 is a program written to communicate with a device connected to intranet 12 according to a set protocol. In this case the protocol may not be a standard protocol, but rather a protocol established for a particular device used at the health care enterprise. A program written in Java implements the protocol and forwards received messages to the enterprise authority manager 40 and native object generator 38 and packages responsive messages for transmission on the intranet 12.

These include, for example, the messages listed in Table 2.

TABLE 2

| Message IN | Message OUT |
|---|---|
| Retrieve list of studies for patient X | Result set containing studies list |
| Retrieve list of series of study X | Result set containing series list |
| Delete study X | Study deletion confirmation or denial |
| Retrieve study X | Result set containing all objects for study X |
| Move study X to DICOM destination Y | Study move confirmation or denial |

The enterprise authority manager 40 provides log-in security services for persons using the system and security information for devices connected to the system. User profile data is stored for each authorized user and device profile data is stored for each authorized device connected to the intranet 12. User profile data includes user name and password as well as any access rules applicable to the user. Device profile data includes the identity of the device, storage priority level of the device, the amount and type of data compression to be applied to images received from the device, the location of the device and the imaging modality (e.g., MRI, CT, PET) of the device. This information is immediately available to the servers 32, 50, 52 and 54 to enable users to log in without delay, and determine if the service being requested has been authorized. For a complete identification of the information stored and used by the enterprise authority manager, reference is made to the configuration guide in Appendix B.

The enterprise authority manager 40 responds to messages from a server 32, 50, 52 and 54 to carry out a log in procedure for the user requesting service from the intelligent image management system 10. It thus provides information to the server which enables the server to form the messages that are sent back to the requesting user during the log-in procedure. In some cases only a user name and password may be required, whereas in other cases information such as account numbers or the like may also be requested.

Figure 5:
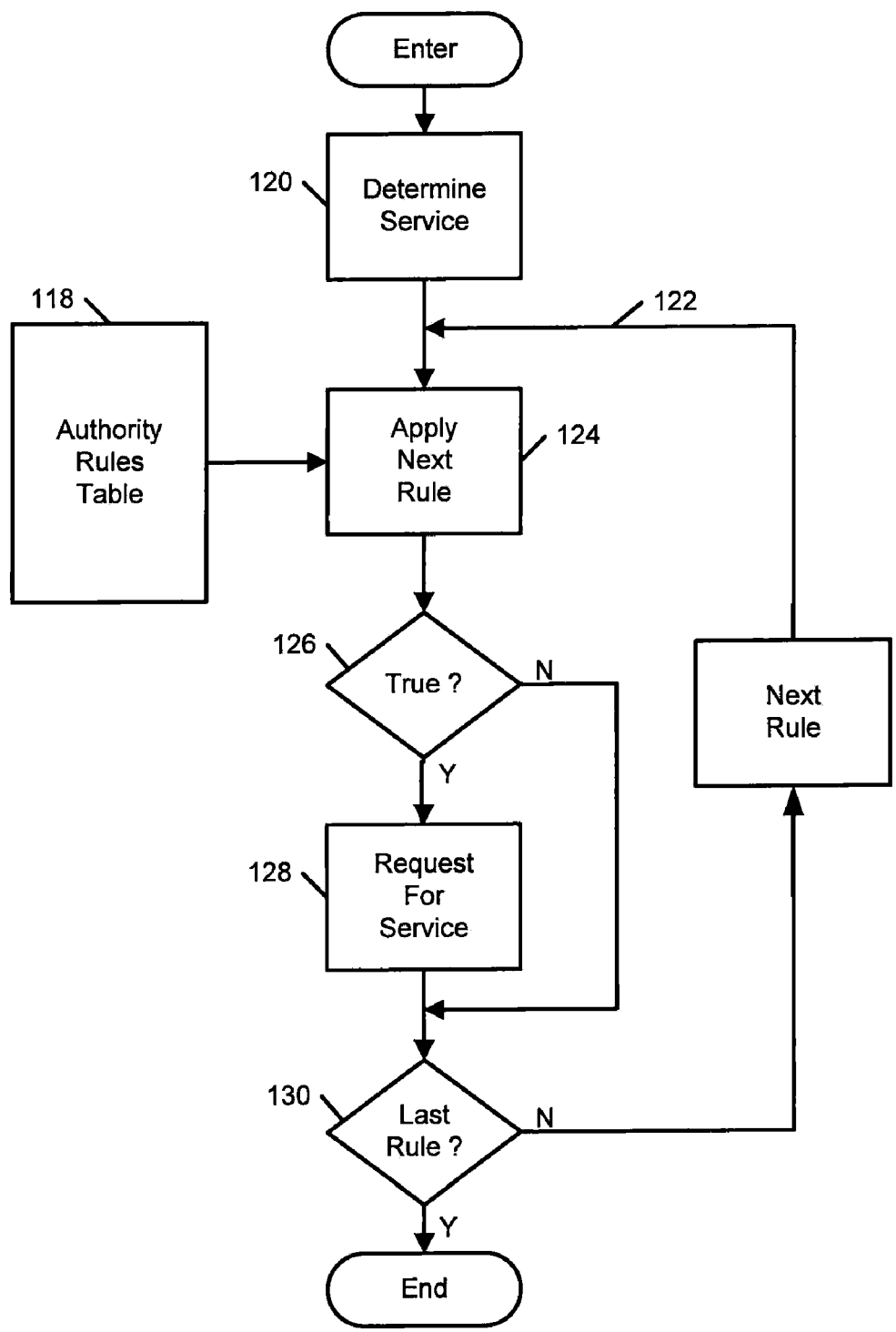
FIG. 5 is a flow chart of the authorization rules processor which forms part of enterprise authority manager in the software in FIG. 4.

In addition, the enterprise authority manager 40 also checks the identity of the particular imaging device involved and performs a number of checks. In DICOM messages, for example, the imaging device is identified by the calling "AE Title" field and this is used to determine if the service is authorized. Referring particularly to FIG. 5, the authority manager includes a rules engine which applies a set of preconfigured rules stored in an authority rules table 118 to the incoming service. As indicated at process block 120, the first step is to identify the device requesting service so that the rules applicable to that device can be identified. A loop is then entered at 122 in which each applicable rule is applied to the requested service at process block 124. If a rule tests true as determined at decision block 126, a request for service is produced at process block 128. In either case a determination is made at decision block 130 if all the authority rules have been processed, and if not, the system loops back to apply the next rule. Rules can thus be stored which limit the type of services a device can request, when the services can be requested, and verify what data types and formats the device is allowed to store/retrieve. In addition, the authority manager may send appropriate data compression instructions to the archive manager 34 based on a stored rule.

The native object generator 38 is a JAVA™ program which receives information from the servers 32, 50, 52 and 54 and forms therefrom JAVA™ objects which are compatible with the system. It is here that information in all its forms is converted into common objects which can be analyzed, processed and stored in the intelligent image management system 10. The reverse is also true—information to be sent to any external device is first converted by the native object generator 38 from the common JAVA™ objects into message information compatible with the particular server 32, 50, 52 or 54 used to communicate with the device.

Figure 7:
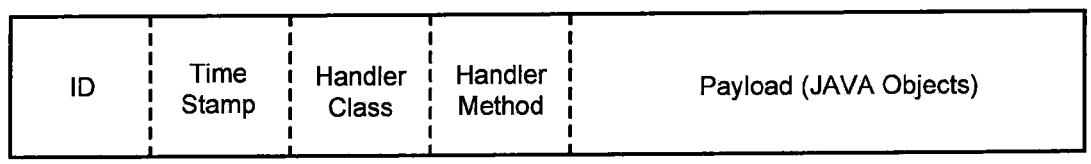
FIG. 7 is a schematic representation of the data structure of a JMS message used by the software of FIG. 4.

The native object generator communicates with a business rules processor 60 and a persistent messaging service 62 using the JAVA™ messages service ("JMS") that conveys the JAVA™ objects as serialized XML messages. As shown in FIG. 7, the JMS messages contain a standard header having a unique message id number and a timestamp that indicates when the message was sent. In addition, the message content includes the class name of a handler and the method name in the handler that is to process the message. Each JMS message also includes a payload comprised of Java objects which more specifically define the service to be provided. At this stage the service is defined rather generally as a request by a device or user for the service type. As will be described below in detail, the business rules processor 60 operates on JMS service request messages to determine precisely what actions are to be performed by the system in response to the requested service. As a result of this analysis, one or more JMS messages are typically produced and sent back to the native object generator 38 for conversion and conveyance to the appropriate server 32, 50, 52 or 54. In addition JMS messages may be produced by the business rules processor 60 and sent to the persistent messaging service 62 where they are stored. Such stored messages may, for example, call for an operation in the future, such as transfer of specific images from RAID storage 18 to tape storage 26 in six months. The persistent messaging service routinely examines the date stamps on stored JMS messages and sends them on the dates indicated to message handlers 64. As described above, a JMS message received by the native object generator 38 from a message handler 64 is converted to a message compatible with one of the servers.

The message handlers 64 are "instantiated" in response to JMS messages produced by the business rules processor 60 or the persistent messaging service 62 or the database management system 44. The instantiated handler will process the message to carry out the indicated service. For example, when a DICOM message requests the storage of images the business rules processor 60 might produce a very specific JMS message indicating that the images are to be stored in RAID storage 18 for the next six months and then they are to be transferred to tape storage 26. The resulting instantiated message handler 64 produces a JMS message for the DICOM server 32 via native object generator 38 to store the images in RAID storage 18. It also produces a JMS message for the data base management system 44 via a database interface 66 to store the corresponding textual metadata in disk drive 14, and it produces a third JMS message for the persistent messaging service 62 indicating the transfer that is to be performed in six months. The business rules processor 60 thus receives general requests for services, and by applying stored business rules that embody enterprise policies and procedures, it issues very specific JMS messages that carry out the service.

Figure 9:
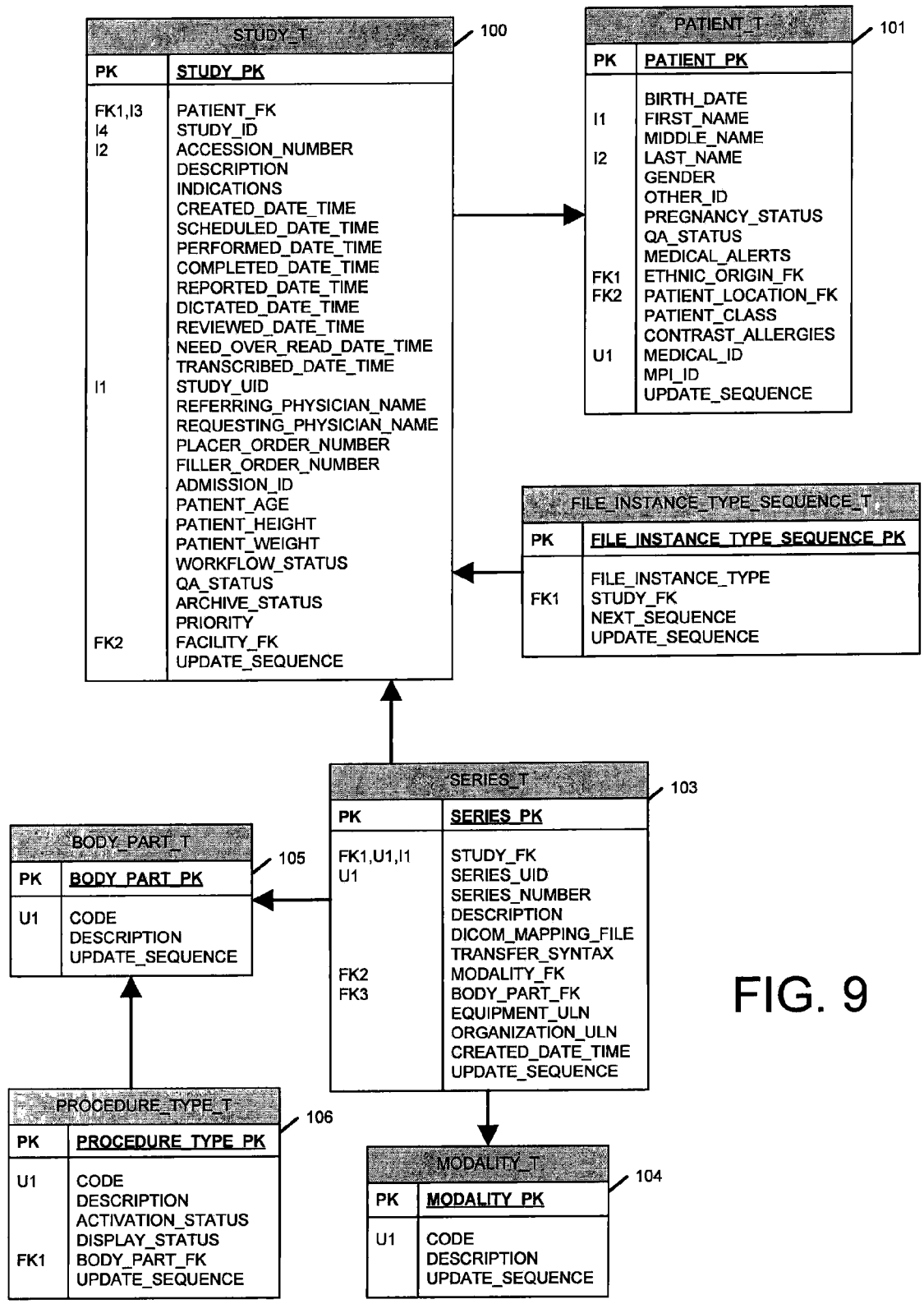
FIG. 9 is a schematic representation of the metadata stored in a database which forms part of the software of FIG. 4.

The database management system 44 is a commercially available system such as the Oracle 9i Database with Oracle XML DB sold by Oracle Corporation. It manages storage and retrieval of all the metadata and other textual or numeric data to be stored in hard disk 14. Such metadata includes the DICOM header information, including patient information, the date when the exam was performed, what type of exam was performed, how long the exam took, the number of images in the exam, and the subject of the exam. Referring particularly to FIG. 9 the metadata stored in the database includes detailed information on the study 100 that was performed, including detailed information on the patient 101. It also includes details on each series 103 that makes up the study, including the modality used 104, the body part 105 that was the subject of the series, and the particular procedure 106 that was employed.

Figure 8:
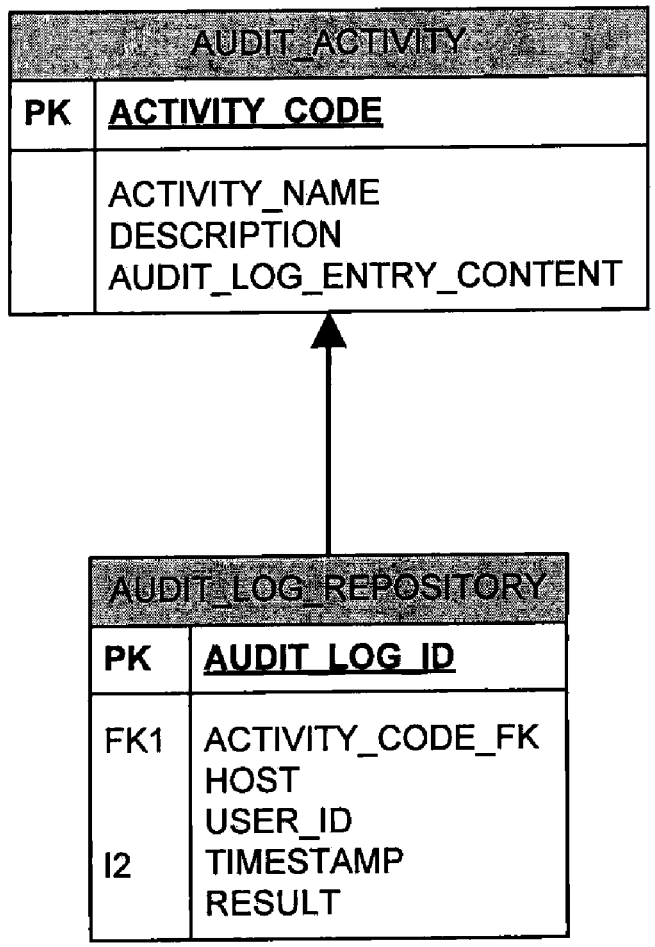
FIG. 8 is a schematic representation of the data structure of an audit log which forms part of the software of FIG. 4.

The data base management system 44 also maintains an audit log 70 which contains information regarding the use and operation of the system 10. This includes how much storage space is required by a study, when it was stored, and how long it took to store the study. It also includes information regarding who and what device accessed information in the system 10. This is done to provide information needed to conform to the federal Health Insurance Portability and Accountability ACT (HIPAA). An entry is made in the audit log 70 each time a request is made for stored metadata. Each entry includes the identity of the requesting user or device, the function that was performed (or attempted), identifying metadata (to identify the data that was accessed), and a date/time stamp. The data structure of the audit log 70 is illustrated in FIG. 8, where "result" is a text field that indicates what transpired during the event, "host"/"user_ID" is the user or device that initiated the event, and "activity_code_FK" indicates the type of service that was requested. Thus, when metadata stored by the database management system 44 is accessed by a device or user, this event is stored in the audit log 70 to provide a record of how the metadata and associated images are managed while resident in the system 10.

The database interface 66 is a JAVA™ program that vends database records into JAVA™ objects so that the complexities of the relational database management system 44 are hidden from the rest of the system. In response to received JMS messages, the database interface 66 properly stores information contained in accompanying objects. For example, a JMS message produced by processor 60 may be handled by storing metadata in the database. The database interface 66 also reads or queries the database using database management system 44, and it produces JMS messages containing JAVA™ objects with information received from the database management system 44. By storing metadata in the relational database, sophisticated queries can be made about patients and about archived images. The information is available on-line even if the associated images are in the tape library 26.

Figure 6:
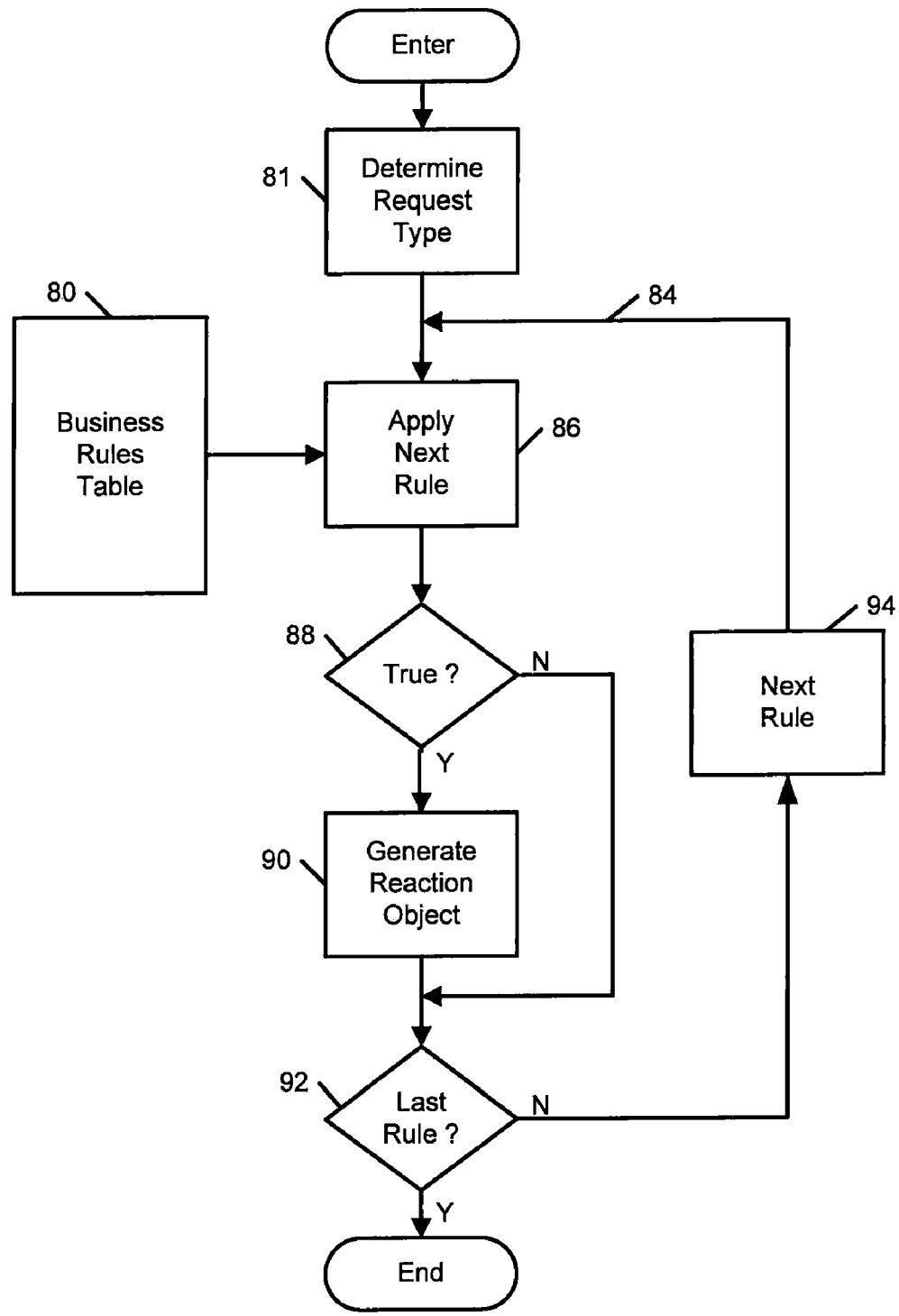
FIG. 6 is a flow chart which illustrates how a business rules processor in the software of FIG. 4 evaluates a request for service using a set of stored rules.

Referring particularly to FIGS. 4 and 6, the business rules processor 60 implements policies established by the health care enterprise to process requests for services from the intelligent image management system 10. These policies are entered into the system as a set of rules which are input from administration workstation 19 (FIG. 1). These rules determine how the system 10 will handle requests to store images, retrieve information regarding patient studies, or update system configuration properties. These rules may be based on such parameters as the size of the study, the identity of the medical device, its modality, or its location within the enterprise. The rules may also be based on the identity of the patient, the procedure performed on the patient, or the particular anatomy concerned in the study. The values of such parameters in any specific request are contained in the payload of the requesting JMS message. The information needed to apply the business rules to the specific request may be obtained from the metadata stored in the system database and the data stored by the authority manager. The rules may also require internal and external environmental parameters such as the time of day and the amount of available storage space. These rules are stored in a business rules table 80.

When a rule tests true, the business rules processor 60 generates a reaction object that directs the action to be taken. The reaction object instantiates a message handler 64 which responds by producing the appropriate messages for system elements as described above. Reaction objects may include, for example, store DICOM object in RAID 18, store DICOM object in DVD library 22, store DICOM object in tape library 26, compress object using JPEG lossy at 10:1 ratio, flush objective from RAID 18, and forward object to DICOM server 32.

Referring still to FIG. 6, when a request in a JMS message is handled by the business rules processor 60, the first step indicated at process block 81 is to determine the type of request being made. There are four categories of requests: store; restore; retrieve and update system configuration properties. A list of services offered in these categories is provided in Appendix A. These service types are sufficiently different that the rules applied to one type of service need not be applied to the other service types. This significantly reduces the number of rules that need to be evaluated for any particular service request.

After the service type is identified, a loop 84 is entered in which each rule in table 80 applicable to that service type is applied to existing parameters at process block 86. This function is performed by a rules engine which applies a defined rule stored in table 80 to XML objects in the JMS message requesting the service. Example rules are listed in Table 3.

TABLE 3

RULE: Select image storage media and assign space based on imaging device, department and facility as identified by image metadata.
Execution Profile:

a. Each device AE TITLE belongs to a specific department & facility at a specific time. Devices may be on a schedule to be share by departments.
b. Each Space is assigned one or more departments/facilities.
c. Lookup AE TITLE'S department and facility in the device profile and determine proper space to allocate for storage.
RULE: Assign image storage media based on procedure type, retrieval characteristics and clinical practices of the organization/organizational unit.
Execution Profile:

A. Each device AETITLE is assigned a finite list of procedure types.
B. Each procedure is configured with specific retrieval characteristics.
C. Each Clinical practice is assigned to an organizational unit.
D. Each organizational unit is composed of one or more departments.
E. Each Space is assigned one or more departments/facilities.
F. Lookup AE TITLE's department and facility in the device profile and determine proper space to allocate for storage.
RULE: Enforce image retention policies of the organization by scheduling and executing moves of older images to lower cost storage media based on the type of procedure and retrieval characteristics.
Execution Profile:

A. Each procedure is configured with specific retrieval characteristics.
B. Each image is associated with a specific procedure,

TABLE 3-continued timestamp, device, series and study.
C. Lookup image retention characteristics using associated procedure, time stamp & AE TITLE.
D. Inject Image Move message into Queue based on retention characteristics.
RULE: Monitor storage media utilization to notify management when utilization reaches planned expansion thresholds; or to reallocate storage capacity executing planned moves based on characteristics of the image data or organizational policy.
Execution Profile:

This rule is performed off of a database trigger that checks for storage availability before and after each archiving operation.
RULE: Monitor system performance response time using time stamp values on service requests and responses with instruction to take actions such as paging system support personnel if response time exceeds a specified service level parameter for a specified period of time.
Execution Profile:

This is performed by running a routine report which summarizes response time and executes the appropriate trigger for notification.
RULE: Monitor system processes to detect system failure, restart back-up processes and/or notify system support personnel in the event of a failure.
Execution Profile:

This is achieved by using a dedicated process monitor which oversees the system processes and is pre-set to take action (such as starting up a back-up process) when any process fails.
RULE: Edit image data and apply storage management rules based on clinical annotations of the diagnostic image. Large image data sets (full body CT, full motion video studies etc) may be archived to low cost, off line media for medical legal records, while segments of the image marked by the reviewing physician as significant to the diagnosis are selected for high availability working storage and clinical distribution.
Execution Profile:

A. Each image is associated with a specific procedure, timestamp, device, series and study.
B. Lookup image retention characteristics using associated procedure, time stamp & AE TITLE.
C. Modify image retention characteristics based on user selection from provided menus. Allow images which appear in a series and which fall between selected images to inherit the characteristics of the modified images.
RULE: Format image presentation based on the display characteristics of the requesting device - desktop PC, hand held wireless device etc.
Execution Profile:

A. Each session is associated with a USER, ROLE & DEVICE.
B. Each data element is mapped to an XML tag.
C. Each Screen is associated with zero or more XML tags and is identified by an XSLT.
D. Each XSLT is mapped to a DEVICE.
E. Each USER is mapped to a ROLE.
F. Each user is mapped to one or more DEVICE'S.
G. Lookup proper screen display elements and properties based on USER, ROLE and DEVICE.
RULE: Normalize presentation of older DICOM images (prior studies) for comparison to current imaging procedures using rules to adjust images presentation based on evolution of the DICOM standard and the age of the prior study.
Execution Profile:

Is the implementation of a rule to handle studies which were taken prior to storage?
RULE: Capture and report User Interface key strokes

TABLE 3-continued to analyze, optimize and tailor UI features to the characteristics and behavior of the user.
Execution Profile:

This is the process of logging each command for each user in a relational table. Standard statistics are compiled based on the relative uses of individual commands. Such statistics could also be compiled based on ROLE, ORGANIZATION, TIME, DATE, STUDY TYPE, etc...
RULE: Capture and report system utilization statistics to automate user billing.
Execution Profile:

This is the process of logging each command for each user in a relational table. Standard statistics are compiled based on the relative uses of individual commands. Such statistics can also be compiled based on ROLE, ORGANIZATION, TIME, DATE, STUDY TYPE, etc...

JAVA™ is the basis for the language used to define the rules, including JAVA's object-oriented features such as common expressions and tests, interfaces, arrays, loops and scope management. Literals are the same syntax as JAVA™, and can be values that are Boolean, integer, floating point, character and string. The syntax of the rule identifier is the same as that of JAVA™, except for reserved keywords.

A rule is comprised of three parts: a header; a condition part; and a reaction part. The header defines the name of the rule, its priority and its packet name. The condition part begins with the word "when" and it defines the conditions that must be met in order for the rule to be true. The reaction part begins with the word "then" and it defines the action or actions that are to be taken when the rule is true. A rule's priority controls the sequence in which rules are executed and the packet name associates a rule with one of the four service types described above. A packet of rules is activated when the service type is determined.

When testing each rule, the business rules processor 60 compares the parameters set forth in the rule with currently existing parameters. Currently existing parameters may include information in stored metadata information contained in the requesting JMS message, in which case the processor 60 determines what action to take based on the metadata. Such metadata parameters are, for example, the imaging modality (i.e., imaging device type), the subject of the image (e.g., abdomen, head, hand), image size and number of images. Currently existing parameters may also include environmental conditions such as the day, the time, available storage space, and the location of the imaging device in the health care enterprise. These environmental conditions are obtained by producing an appropriate JMS message requesting the information from the system clock (not shown in the drawings), the archive manager 34, the enterprise authority manager 40 or the database management system 44. In this case the processor 60 determines what action to take based on the current condition of the image management system 10 and/or the health care enterprise. Of course, rules often base actions on both the metadata and environmental conditions.

If a rule tests true as indicated at decision block 88, a reaction object is generated at process block 90. If the rule tests false, no reaction object is generated. As described above, reaction objects(s) identified by the rule are used to produce one or more JMS messages which results in the appropriate operations being performed. Such reaction objects include, for example, store an image object in RAID 18, or store an image object in DVD library 22, or store an image object in tape library 26. When the last active packet rule stored in table 80 has been tested, as determined at decision block 92, business rules processing is completed for the current service request. Otherwise, the business rules processor 60 loops back through process block 94 to apply the next rule.

It should be apparent that the business rules processor 60 collects the logic necessary to make all the business decisions regarding image storage and management in one, easily maintainable place. More importantly, it enables a user-friendly graphic interface to be written which enables institutional policy to be implemented by the system. This graphical user interface is downloaded to the workstation 19 to provide an intuitive, user-friendly interface which enables the rules 80 to be created and edited.

APPENDIX A

Service Request Message Objects

Generic
   OpenStudySessionHandler.endStudySession
   OpenStudySessionHandler.openStudy
   JobHandler.runJobs
   JobUIHandler.deleteJob
   JobUIHandler.fetchJobs
   JobUIHandler.updateJob
   LogStoreHandler.createAuditEntry
   EventHandler.cleanNotificationQueue
   EventHandler.processEvent
   EventHandler.processNotification
   PerformanceHandler.persistMetrics
   JobUIHandler.fetchAllJobs
   FlushHandler.flushLocation
   FlushHandler.nightlyFlush DICOM
   DICOMStoreHandler.beginStore
   DICOMStoreHandler.commit
   DICOMStoreHandler.commitStorage
   DICOMStoreHandler.createSCJob
   DICOMStoreHandler.endStore
   DICOMStoreHandler.getFileNameGenerator
   DICOMStoreHandler.processCloseStudyJob HL/7
   HL7Add UpdatePatientHandler.addPatient
   HL7Add UpdatePatientHandler.updatePatient
   HL7ClientHandler.validatePatientInfo
   HL7ClientHandler.validatePatientQAInfo
   HL7MergeHandler.unMergePatients
   HL7QueryHandler.fetchPatients
   TMHL7MergeHandler.mergePatients Archive
   ArchiveHandler.archiveBag
   ArchiveHandler.retrieveArchivedFiles
   ArchiveHandler.retrieveBag Query
   QueryHandler.fetchDataElements
   QueryHandler.fetchFileInstances
   QueryHandler.fetchPatients
   QueryHandler.fetchPatientsAndStudies
   QueryHandler.fetchQAIssues
   QueryHandler.fetchQAPatients
   QueryHandler.fetchQAStudies
   QueryHandler.fetchSeries
   QueryHandler.fetchSeriesFiles
   QueryHandler.fetchStudies
   QueryHandler.fetchPerformanceMetrics
   QueryHandler.fetchQAIssuesFilter
   UIQueryHandler.fetchPatients
   UIQueryHandler.fetchSeries
   UIQueryHandler.fetchStudies Metadata
   PersistMetadataHandler.moveFileInstances
   PersistMetadataHandler.moveSeries
   PersistMetadataHandler.persistPatient
   PersistMetadataHandler.persistSeries
   PersistMetadataHandler.persistStudy
   DeleteMetadataHandler.deletePatient
   DeleteMetadataHandler.deleteSeries
   DeleteMetadataHandler.deleteStudy
   PersistMetadataHandler.mergePatients
   QAMetadataHandler.deleteStudyQA
   QAMetadataHandler.resolveStudyQA
   QAMetadataHandler.storeStudyQA
   PersistMetadataHandler.moveStudies
   PersistPatientQAHandler.deletePatientQA
   PersistPatientQAHandler.deletePatientQAStudy
   PersistPatientQAHandler.persistPatientQAStudy

APPENDIX B

Confirmation Guide

DicomClientIdentifierClass
   Each piece of equipment, or modality, that wishes to connect as an SCU or Client will need to have a DicomClientIdentifier object set up.

| DicomClientIdentifierClass | |
| --- | --- |
| AETitle | (O) The Application Entity Title for the modality. |
| SCUTransferSyntaxList | (O) the list of Transfer Syntaxes this modality supports. The order of the list indicates selection preference in the DICOM Association |
| SCUSOPClassList | (O) the list of SOP Classes this modality supports. |
| MaxPDUSize | (O) the maximum packet size this modality supports. |

DicomServerIdentifierClass
   Each Dicom Listener (or DicomServer), will need to have a DicomServerIdentifier Class object set up to specify it's Dicom related settings. Also, each piece of equipment, or modality, that will connect as an SCU or Client will need to have a DicomServerIdentifier object set up. In other words, an entry will be created here for equipment that wishes to be an SCP.

| DicomServerIdentifierClass | |
| --- | --- |
| AETitle | (O) The Application Entity Title for the modality. |
| ImplClassUID | (Fixed) The implementation class UID of the Institution that is creating images for distribution in the industry. This UID has the world wide granted institutional UID with a unique trailer |

-continued

| DicomServerIdentifierClass | |
|---|---|
| | that the institution assigns. It is initially set to the issued UID to indicate the software that uses it. It can be changed in accordance with the policy found in PS3.7 part of the DICOM standard. It is recommended that the value NOT be changed. |
| ImplVersion | (Fixed) The implementation version of the software that creates images for distribution to the industry. This value is defined in the system to indicate the version of the distributed software. It is recommended that the value NOT be changed. |
| Port | (O) the port the DicomListener will be listening on. |
| MaxPDUSize | (O) the maximum packet size the server will support. |
| SCPSOPClassList | the list of SOP Classes this Dicom Listener supports as an SCP. |
| SCPTransferSyntaxList | (O) the list of Transfer Syntaxes this Dicom Listener supports as an SCP. |

DicomEquipmentClass

Each system/equipment that will interact as an SCU or SCP will need to have an entry set up inside DicomEquipmentClass. The entry can contain:

| DicomEquipmentClass | |
|---|---|
| Host | (M) host name of the modality |
| DicomIdentifierULN | (M) The Unique Logical Name (ULN) of the DicomClientIdentifierClass or DicomServerIdentifierClass entry for this modality |
| Description | (O) A textual description of the modality. |
| OrganizationULN | (M) The OrganizationClass Unit the modality belongs to OverridingGroupName - (U) not currently used. |
| AllowNewStudies | (O) A boolean that authorizes this modality to create a new study. |
| AllowAppendToExistingStudies | (O) A boolean that authorizes this modality to append to an existing study. Value = true/false |
| DICOMMappingFile | (O) If the modality is sending meta-data in non-standard locations, a mapping file is used to tell TI²m where to get the information. |
| AllowCEcho | (M) A boolean that authorizes this modality to perform a C-Find. Value = true/false |
| AllowCStore | (M) A boolean that authorizes this modality to perform a C-Store. Value = true/false |
| AllowCMove | (M) A boolean that authorizes this modality to perform a C-Move. Value = true/false |
| AllowNAction | (M) A boolean that authorizes this modality to perform an N-Action request. Value = true/false |
| PatientMatchingCriteriaList | A list of string values that represent the fields in the database that you want to be able to match against RIMS. Valid values: FirstName, MiddleName, LastName, BirthDate, Gender |
| StudyMatchingCriteriaList | A list of string values that represent the fields in the database that you want to be able to match against incoming studies. Valid values: StudyID, PlacerOrderNumber, FillerOrderNumber |
| StorageCommitULN | (O) This points to a StorageCommitmentClass object to get storage commitment configuration values. |
| EquipmentID | (O) The internal (clinic) equipment identifier. |
| StudyClosePolicy | (O) |
| StudyCloseTimerValueInMinutes | (O) |
| DicomMapULN | (O) |
| Status | (O) A Boolean |
| PerformStorageVerification | (O) A Boolean |
| LocationList | (O) This is a list of LocationULNs in which IODs are stored within the system. The LocationClass contains these entries that further describes the format for IODs. |
| NumberAssociationsAllowed | (M) An Integer indicating number of associations this equipment can have with TIIM at a given time. |

LocationClass

There are multiple internal locations that can store IODs in the system and each of them requires a set of attributes that describe the format and processing required for IODs stored in each location. Each location that stores IODs must have an entry set up inside this LocationClass container. The entry will be a Unique Logical Name of the format (<xxxx>LocationULN). The entry can contain:

| LocationClass | |
|---|---|
| LocationType | (M) "O" = Online, "N" = Nearline, "A" = AutoForward |
| Description | (O) a textual decription of this location class |
| ModalityCompressionList | (O) |
| AutoForwardAETitle | (O) |
| OnlineRetentionTimeInMonths | (O) The number of months that the information should remain in this location. |

ModalityCompressionClass

This container matches IODs from a specific modality with the desired storage format or compression characteristics that an organization would like to see. Each modalityCompression pairing must have a set up inside ModalityCompressionClass. The entry will be a Unique Logical Name of the format (<xxxx>ModalityCompressionULN). The entry can contain:

| ModalityCompressionClass | |
|---|---|
| OrganizationULN | (O) |
| Modality | (O) |
| CompressionAlgorithmULN | (O) |

CompressionAlgorithmClass

Each entry in this class describes a form of compression that can be performed on an IOD. There are different attributes that need to be defined to correctly setup the compression that is performed. The (C=<transferSyntax>) conditional entries indicate the dependency of the attribute on the contents of the transferSyntax attribute. The entry can contain:

| CompressionAlgorithmClass | |
|---|---|
| TransferSyntax | (M) |
| 1.2.840.10008.1.2 or LITTLEENDIAN | |
| 1.2.840.10008.1.2.1 or LITTLEENDIANEXPLICIT | |
| 1.2.840.10008.1.2.2 or BIGENDIANEXPLICIT | |
| 1.2.840.10008.1.2.4.50 or JPEGBASELINEPROCESS1 | |
| 1.2.840.10008.1.2.4.51 or JPEGEXTENDEDPROC2AND4 | |
| 1.2.840.10008.1.2.4.57 or JPEGLOSSLESSPROC14 | |
| 1.2.840.10008.1.2.4.70 or JPEGLOSSLESSPROCFIRSTORDERPREDICT | |
| 1.2.840.10008.1.2.5 or RLE | |
| GenHuffman | (C = JPEGLOSSLESSPROCFIRSTORDER PREDICT or JPEGLOSSLESSPROC14; D = TRUE) This true/false Boolean entry will cause the compression routine to generate an optimized Huffman entropy table for each IOD during the compression if the value is true which is the default. |
| Selector | (C = JPEGLOSSLESSPROC14; D = 4). This is a number between 1 and 7 that determines the prediction selector to be used in the lossless compression process 14. The best compression appears to occur with this set to 4. |
| RangeComp | (O) (C = JPEGEXTENDEDPROC2AND4; D = 7) This factor is used internally to perform a couple of different preprocessing actions on an IOD that has the "bitsStored (0028,0101)" header tag greater that 12. The Lossy compression is limited to images that have a dynamic range of vales less than 12 bits or 4096 values. The recommend value here is 7 which enables all three preprocessing rules. It only applies to images that have more than 12 bits used to store pixel values. |
| QualityFactor | (C = JPEGEXTENDEDPROC2AND4 or JPEGBASELINEPROCESS1; D = 75) This defines the level of quality to apply during the Lossy compression process. The value is between 1 and 99 where a value of 63 produces a compression ratio of about 10:1 and a value of 23 produces a compression ration of about 20:1. The higher the compression ratio (smaller the quality value) will cause less quality in the resulting image. |
| genNewUID | (O; D = FALSE) This can be used to defeat the standard requirement to create a new SOPInstanceUID for every IOD created or derived. The default (false) is to NOT generate a new UID for the processed (compressed) IOD, but to retain the UID of the full fidelity original IOD. |

OrganizationClass

This configuration class describes the high level groupings/hierarchy. It allows the installer to create a new group and to attach the group to its parent group. Although this infrastructure has been set up, not much is being done with this yet. Examples:

| USOrgULN | |
|---|---|
| USOrgULN | |
| Description | (O) Text description of the organizational unit. Example: Ultrasound |
| ParentULN | (O) Parent organizational unit Example: RadiologyOrgULN |
| OverridingGroupName | (O) US1Group |
| LocationList | (O) This is a list of on-line and auto forward locationULNs for storage by equipment in this organization. The LocationClass contains these entries that further describes the format for IODs. |
| AccessionNumberMatchingULN | (M) This is the ULN that points to the correct AccessionNumberMatchingClass |

| RadiologyOrgULN | |
|---|---|
| RadiologyOrgULN | |
| Description | (O) Example: Radiology Department |
| ParentULN | (O) Example: EnterpriseOrgULN |
| OverridingGroupName | (O) Example: RadiologyGroup |
| LocationList | (O) This is a list of on-line and autoforward locationULNs for storage by equipment in this organization. The LocationClass contains these entries that further describes the format for IODs. |
| AccessionNumberMatchingULN | (M) This is the ULN that points to the correct AccessionNumberMatchingClass |

HL7SourceClass (multiple instances) contains information about HL7 clients.

This way we are able to customize properties per client. Each source contains:

| HL7SourceClass | |
|---|---|
| SendingFacility | (O) The HL7 MSH field "SendingFacility". Usually is a string containing name of the sending facility. |
| PatientMatchingCriteria | (O) The ULN that we should use to determine patient matching criteria for ADT ^ A04 and ADT ^ A08. Look at HL7SourcePropertiesClass. |
| AcceptNewPatients | (O) this has a value of True/False, indicating whether to add new patients or not for ADT ^ A04 and ADT ^ A08 messages. |

HL7SourcePropertiesClass (multiple instances) contains instances of source configurations. These instances currently only contain:

| HL7SourcePropertiesClass | |
|---|---|
| PatientMatchingCriteria List | (O) contains "MEDICAL_ID", "FIRST_NAME", "LAST_NAME" etc indicating which columns in the PATIENT table should be looked at before deciding up equality of two patients. |

QAClass

This class is used by the HL7Validation to RIMS. The parameters here specify how to check TEAM values against the values from RIMS.

| QAClass | |
|---|---|
| IgnoreCase | (O) Should the Patient Matching ignore case when looking at fields (values: TRUE/FALSE) |
| IgnoreTrailingAndLeading Spaces | (O) Should the Patient Matching ignore trailing and leading spaces when looking at the fields. (values: TRUE/FALSE) |
| AutoCorrectContent | (O) Should the Patient Matching autocorrect content from RIMS if the content is not Patient Matching Criteria (values: TRUE/FALSE) |
| QAQueueSortOrder | (O) Determines the default sort order for the QA Issue Queue UI screen. Valid values include: DESCRIPTION, PATIENT_ID, PATIENT_NAME, STUDY_DATE, |

HL7ClientClass

Contains settings for instances of HL7 Clients. Under each instance, the following entries may be modified:

| HL7ClientClass | |
|---|---|
| Description | (O) description of the HL7 client |
| Host | (O) the hostname of the client |
| MessageDefinitionFile | (O) the vmd file that contains the message tables grammar for this client (usually in the config directory) |
| RetryTimeout | (O) amount of time before the HL7 message is retried at the client if there was a failure |
| Port | (O) the port of the client machine we're trying to connect to |
| SendingApplication | (O) One of the parts of the HL7 message |
| SendingFacility | (O) One of the parts of the HL7 message |
| ReceivingApplication | (O) One of the parts of the HL7 message |
| ReceivingFacility | (O) One of the parts of the HL7 message |

HL7ServerClass (Singleton) contains properties of HL7 Server, namely:

| HL7ServerClass | |
|---|---|
| IPAddress | (O) the IP address/host the server startup should bind to (is relevant if you have a server with multiple network cards and only one of them is used by the outside clients that connect to it. This saves some kernel time by not binding up a port to all interfaces). Always make sure this is accurate. |
| Port | (O) the port that HL7 clients would connect to TI$^2$m. Default is 4080. |

| HL7ServerClass | |
|---|---|
| MessageDefinitionFile | (O) the Interfaceware Chameleon Message Definition File that contains segment grammer and table settings based on which the HL7 Server would work. This file usually has an extension of ".vmd". Default is to look for Server.vmd. |
| Backlog | (O) this indicates the backlog for the TCP/IP server socket. This would limit number of TCP/IP connections in the listener queue that are to be processed. Default is 30. |

Specific Configuration Discussions
  Setting up the Compression Options
  In LDAP, the Compression of Stored objects is defined within a LocationClass entry by the modalityCompressionList attribute. If this attribute is empty or not defined, compression will not be performed at this storage location.
  DicomEquipmentClass
    This Class can contain a LocationList entry that references entries in the LocationClass table
  OrganizationClass
    This Class can contain a LocationList entry that references entries in the LocationClass table
  GeneralClass
    This Class can contain a LocationList entry that references entries in the LocationClass table.
    GeneralClass
      FileTypeSequenceIncrement=400
      OrganizationGroup=Enterprise
      LocationList=onlineLocation1Uln
  LocationClass
  Entries in this Class are defined in the LocationList attribute in any of the Classes DicomEquipmentClass, OrganizationClass, or GeneralClass. If LocationList is not defined at the DicomEquipmentClass level, TI$^2$m looks to the OrganizationClass level, and then at the GeneralClass to find a LocationList. The LocationList is a list of LocationClass Unique Logical Name (ULN) entries that describe the places that data is stored for the Equipment, Organization, or Everywhere else.
  Within a LocationClass entry, the modalityCompressionList attribute is a list of ModalityCompressionClass ULNs that apply to data stored at that location. The other entry locationType defines if the location is OnLine "O", AutoForward "A", or Nearline "N"
  For example, you wish all CT image objects to be compressed using lossless JPEG technique and all MR images to be stored using the JPEG Lossy compression, and all Secondary Capture images to be stored Implicit Little Endian. Then you need to define at least two ModalityCompressionClass entries each with a ULN.
  LocationClass
    onlineLocation1Uln
      Description=Lossless copies
      onlineRetentionTimeInMonths=12
      locationType=O
      ModalityCompressionList=MR_RadiologyOrgUL
        N^CT_RadiologyOrgULN
    onlineLocation2Uln
      Description=Lossy copies
      onlineRetentionTimeInMonths=24
      locationType=O ModalityCompressionList=MR_RadLossyUL
    NCT_RadLossyULN
    archiveLocation1Uln
        Description=Original copy archive location
        locationType=N
ModalityCompressionClass This Class has three attributes in each of its entries. They are modality, organizationULN and compressionAlgorithmULN.

The modality entry should be quite obvious (CT, MR, SC, etc.)

The organizationULN entry points into entries in the OrganizationClass table.

The compressionAlgorithmULN is the ULN of a single CompressionAlgorithmClass entry.

ModalityCompressionClass
    MR_RadiologyOrgULN
        modality=MR
        organizationULN=RadiologyOrgULN
        compressionAlgorithmULN=jpegLossyUln
    CT_RadiologyOrgULN
        modality=CT
        organizationULN=RadiologyOrgULN
        compressionAlgorithmULN=jpegLosslessUln
    MR_RadLossyULN
        modality=MR
        organizationULN=USOrgULN
        compressionAlgorithmULN=jpegLossyUln
    CT_RadLossyULN
        modality=CT
        organizationULN=USOrgULN
        compressionAlgorithmULN=jpegLossyUln
    MR_EnterpriseOrgULN
        modality=MR
        organizationULN=EnterpriseOrgULN
    CT_EnterpriseOrgULN
        modality=CT
        organizationULN=EnterpriseOrgULN
CompressionAlgorithmClass This Class has two different fundamental types of entries. An entry defines the type of JPEG pixeldata encapsulation to be used on image objects stored. Each entry provides a holder for the individual characteristics to be used during compression. There is the Lossless type and the Lossy type of entry.

The Lossless CompressionAlgorithmClass entry has three effective attributes that can be defined. If the attribute is not defined, a recommended default value is used internally. The attributes of the Lossless entries are transferSyntax, selector, and genHuffman.

The Lossy CompressionAlgorithmClass entry has three effective attributes that can be defined. If the attribute is not defined, a recommended default value is used internally. The attributes of the Lossy entries are transferSyntax, quality, and rangeComp.

It is OK to define all five attributes in either type of entry because the values do not collide in their usage.

The transferSyntax entry defines the type of compression that should be used. The choices:
    "1.2.840.10008.1.2.4.57" [JPEG_14 Lossless]
    "1.2.840.10008.1.2.4.51" [JPEG Extended (Process 2 & 4)]
    "1.2.840.10008.1.2.4.70" [JPEG Lossless (Process 14, Selection Value 1)]
    "1.2.840.10008.1.2.4.50" [JPEG Baseline]
        (This is redundant to 4.51 Process 2 which is for 8 bit images. TI$^2$m is incorrect at this time if the image is more than 8 bits. In this latter case, we use 4.51 but tag the image as 4.50)
    "1.2.840.10008.1.2.5" [RLE Lossless]
        (This is broken and should be avoided)
    "JPEGLOSSLESSPROC14"
        [1.2.840.10008.1.2.4.57=JPEG_14 Lossless]
    "JPEGEXTENDEDPROC2AND4"
        [1.2.840.10008.1.2.4.51=JPEG Extended (Process 2 & 4)]
    "JPEGLOSSLESSPROCFIRSTORDERPREDICT"
        [1.2.840.10008.1.2.4.70=JPEG Lossless (Process 14, Selection Value 1]
    "JPEGBASELINEPROCESS1" [1.2.840.10008.1.2.4.50]
    "RLE" [1.2.840.10008.1.2.5]

Use of the second five textual versions is allowed but this will cause a small performance impact. The choices are listed in the recommended order of preference. There is no default choice.

The selector value is really only applicable to the "1.2.840.10008.1.2.4.57" Lossless encoder. Current experience shows that selector "4" (the default) creates the highest lossless compression ratio. Setting selector to "1" causes effectively a "1.2.840.10008.1.2.4.70" Lossless encoding The quality entry is a number that drive the lossy encoding process. The higher the number the less lossiness occurs or the better the image quality. A value of 63 seems to produce a compression ratio of between 7:1 and 11:1 roughly. A value of 23 results in about a 20:1 ratio. The number is fudged internally for RGB images to try an maintain this relationship of quality to compression ratio.

The genHuffman entry is a Boolean (true/false) entry used in the Lossless encoder and defaults "true". Experience shows that generating the Huffman table is either faster or of no performance impact and produces a better compression ratio.

The rangeComp entry is an integer value that can be set to 0, 1, 3, 5, or 7. The other values (2, 4, and 6) have no effect.

The rangeComp entry was created to allow the Lossy compression of images that say they have pixels that are 16 bit values ((0028,0100) bitsStored) in the header. It is known that most CT images really have a dynamic range of 12 bits and the value 16 is used to allow the pixels to be stored in 2's complement notation.

The rangeComp entry is only used if the "bitsStored" (0028, 0100) entry is greater than 12. If it is greater than 12, the rangeComp entry's least significant bit ("1") allows the logic to perform a scan of all the pixels to determine the really dynamic range of the image. During this initial scan, all pixels that are equal to the "pixelPaddingValue" (0028,0120) are replaced with the value 0. This "pixelPaddingValue" (0028, 0120) is used in many CT images to define the area outside of the real data region of the image. If the range is determined to be less than 12 bits after coercion and all the pixels are now between 0 and 4095 in value, the image can be Lossy compressed.

If the dynamic range is still greater than 12, the next two bits provide two levels of coercion on the pixels to reduce the range to 12 bits and therefore enable Lossy compression. I mean lossy is lossy and why not try further. OK? The "2" bit or the "4" bit will enable a second scan of all the pixels to correct for either of two pixel conditions.

During the first full scan of the image the "min_pix" and "max_pix" values are determined. If the "min_pix" is zero, and if rangeComp has the "2" bit set, the whole image will be scanned a second time to find all pixels that have a value of the "max_pix" and these pixels will set to the value 4095. Some screensave images use a very large value to store graphics burned into the image.

An alternative coercion tests is where the "min_pix" was found negative during the first pixel scan. If rangeComp has the the "4" bit set, all pixels equal to the "min_pix" value will be set to 0 during the second pixel scan. This is a common problem with CT images in the corner areas when the "pixelPaddingValue" (0028,0120) element is undefined. After all the pixel scans are done, the dynamic range is tested for less than 4095 allowing for Lossy compression with minimum impact to graphic or background content.

The isLossy flag is a Boolean value indicating whether this compression algorithm is lossy.
    CompressionAlgorithmClass
        jpegLosslessUln
            transferSyntax=1.2.840.10008.1.2.4.57
            selector=4
            genHuffman=true
        jpegLossyUln
            transferSyntax=1.2.840.10008.1.2.4.51
            quality=63
            rangeComp=7

We claim:

1. An image management system connected to receive messages over a healthcare enterprise network, the image management system comprising:
    a plurality of storage devices, where at least one of the storage devices has a cost characteristic that differs from the cost characteristics of the other storage devices;
    means for receiving, over the network, a message that includes:
        a request category, wherein the request category includes at least one of a store category, a retrieve category, and a restore category; and
        at least one parameter extracted from metadata that includes information related to at least one of acquired image data, stored image data, and patient information;
    a business rules processor communicatively coupled to the means for receiving that is operable to:
        identify, from the received message, a set of stored rules related to the request category;
        determine at least one rule in the identified set of stored rules that is satisfied by processing the at least one parameter in the received message in accordance with each rule in the identified set of stored rules; and
        produce a reaction object for the satisfied rule; and
    archiving means responsive to the produced reaction object to:
        store at least one of image data and patient information corresponding to the metadata in at least one of the plurality of storage devices when the satisfied rule is related to the store category;
        retrieve at least one of image data and patient information corresponding to the metadata from at least one of the plurality of storage devices when the satisfied rule is related to the retrieve category; and
        transfer at least one of image data and patient information corresponding to the metadata from at least one of the plurality of storage devices to another of the plurality of storage devices when the satisfied rule is related to the restore category.

2. The image management system as recited in claim 1 which includes a database management system responsive to the reaction object produced by the business rules processor to store the metadata in a database when the satisfied rule is related to the store category.

3. The image management system as recited in claim 1 which includes an enterprise authority manager coupled to the means for receiving, the enterprise authority manager storing information on a plurality of image producing devices authorized to store images in the image management system, and being operable to determine if a message received over the network is from an authorized image producing device.

4. The image management system as recited in claim 3 in which the enterprise authority manager stores information indicative of the data type appropriate for an authorized image producing device.

5. The image management system as recited in claim 4 in which the means for receiving also includes means for receiving messages over the network from users requesting access to stored images and associated stored metadata, and in which the enterprise authority manager stores information indicative of authorized users.

6. The image management system as recited in claim 5 in which the enterprise authority manager is operable to deny access to unauthorized users.

7. The image management system as recited in claim 1 in which the business rules processor includes a plurality of stored rules which identify different actions to be performed and each identifies a set of parameters which must be present for the rule to be satisfied.

8. The image management system as recited in claim 7 in which one of said parameters is the identity of the image producing device.

9. The image management system as recited in claim 7 in which one of the parameters is the location of the image producing device.

10. The image management system as recited in claim 7 in which the image producing devices include medical imaging systems and one of said parameters is the imaging modality.

11. The image management system as recited in claim 10 in which one of said parameters is the subject of the image.

12. The image management system as recited in claim 7 in which one of said parameters is the subject of the image.

13. The image management system as recited in claim 1 in which the metadata further includes information related to at least one of the patient, a patient study, a series, a patient body part, an imaging modality, and a procedure type.

14. The image management system as recited in claim 2 which includes an audit log stored in the database and the database management system is operable to record in the audit log information related to the metadata stored in the database.

15. The image management system as recited in claim 14 in which the information related to the metadata includes the dates on which the metadata is accessed and the identities of requesting users.

16. An image management system connected to receive messages which contain image data and associated metadata from an image producing device, which comprises:
    a plurality of storage devices, where at least one of the storage devices has a cost characteristic that differs from the cost characteristics of the other storage devices;

means connected to receive the messages and a request message, wherein the request message includes a storage request category;

processor means coupled to the means for receiving and being operable to examine metadata in received messages and parameters in a set of stored rules related to the request category to determine in which of said plurality of storage devices the associated image data should be stored when the set of stored rules is related to the store category; and means for storing the associated image data in the storage device determined by the processor means.

17. The image management system as recited in claim 16 in which one of the plurality of stored rules identifies one of said plurality of storage devices and one or more parameters that must be satisfied to store image data in that storage device.

18. The image management system as recited in claim 17 in which one of said parameters is the subject of the image and the metadata indicates the subject of its associated image data.

19. The image management system as recited in claim 17 which includes a workstation coupled to the processor means for enabling a user to input and edit said stored rules.

20. The image management system as recited in claim 17 in which:

the request message further includes a restore request category;

the processor means is operable, when stored rules related to the restore request category are satisfied, to produce a subsequent request message indicating that the image data is to be transferred to another one of said storage devices at a later time; and the image management system further includes:

a persistent messaging service coupled to the processor means and being operable to store said message to be acted upon at a later time; and means for acting on the stored message at said later time to transfer said image data to said another one of said storage devices.

21. The image management system as recited in claim 16 which includes a database management system coupled to the processor means and being operable to store the metadata in a database.

22. The image management system as recited in claim 21 which includes an audit log stored in the database and the database management system is operable to record in the audit log information related to the metadata stored in the database.

23. The image management system as recited in claim 22 in which the information related to the metadata includes the date on which the metadata is accessed and the identity of the requesting user.

24. A method for storing images produced by a plurality of medical imaging devices located in a healthcare enterprise, the steps comprising:

a) electronically sending, to an image management system:
   i) an image produced by a medical imaging device;
   ii) metadata associated with the image, wherein the metadata includes information about the image; and
   iii) a message that includes a request category, wherein the request category includes at least one of a store category, a retrieve category, and a restore category;

b) storing a set of rules in the image management system which indicates how images for the healthcare enterprise are to be stored, wherein the set of rules includes rules corresponding to the store, retrieve, and restore categories;

c) evaluating a stored rule selected from the request category by examining the metadata associated with each image received by the image management system;

d) transferring the image in a manner indicated by a rule which is evaluated as satisfied; and e) storing the metadata associated with the image in a database.

25. The method as recited in claim 24 in which step c) is performed by comparing parameters in the selected stored rule with information in the metadata associated with the image to determine if the rule is satisfied.

26. The method as recited in claim 25 in which the parameters include the modality of the medical imaging device that produced the image.

27. The method as recited in claim 25 in which the parameters include the location within the healthcare enterprise of the medical imaging device that produced the image.

28. The method as recited in claim 25 in which the parameters include the subject matter depicted in the image.

29. The method as recited in claim 24 in which step d) includes storing the image in one of a plurality of different storage devices, wherein at least one of the storage devices has a cost characteristic different than the cost characteristics of the other storage devices.

30. The method as recited in claim 24 which includes:
   f) changing the stored rules to reflect a change in the image storage policy of the healthcare enterprise.

31. The method as recited in claim 30 in which step f) is performed by:
   i) entering rule data at a workstation; and
   ii) electronically sending the rule data to the image management system.

32. The method as recited in claim 24 in which step d) includes:
   storing the image in one of a plurality of different storage devices; and
   storing a message that includes a request category, which indicates the image is to be transferred to another of said storage devices at a later time.

* * * * *

UNITED STATES PATENT AND TRADEMARK OFFICE
CERTIFICATE OF CORRECTION

PATENT NO.        : 7,583,861 B2                                      Page 1 of 1
APPLICATION NO.   : 10/720799
DATED             : September 1, 2009
INVENTOR(S)       : Hanna et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1350 days.

Signed and Sealed this

Fourteenth Day of September, 2010

David J. Kappos
*Director of the United States Patent and Trademark Office*